United States Patent
Ferreira et al.

(10) Patent No.: US 11,944,095 B2
(45) Date of Patent: Apr. 2, 2024

(54) SUBSTRATE FOR EFFICIENT USE IN SANITIZING AND DISINFECTING

(71) Applicant: Suominen Corporation, Helsinki (FI)

(72) Inventors: Rui Ferreira, Longmont, CO (US);
Muralidhar Lalagiri, Vernon, CT (US);
Avinav G. Nandgaonkar, Vernon, CT (US)

(73) Assignee: Suominen Corporation, Helsinki (FI)

( * ) Notice: Subject to any disclaimer, the term of this patent is extended or adjusted under 35 U.S.C. 154(b) by 58 days.

(21) Appl. No.: 16/603,279

(22) PCT Filed: Apr. 5, 2018

(86) PCT No.: PCT/FI2018/050244
§ 371 (c)(1),
(2) Date: Oct. 7, 2019

(87) PCT Pub. No.: WO2018/185374
PCT Pub. Date: Oct. 11, 2018

(65) Prior Publication Data
US 2021/0106003 A1    Apr. 15, 2021

Related U.S. Application Data

(60) Provisional application No. 62/481,715, filed on Apr. 5, 2017.

(51) Int. Cl.
| | | |
|---|---|---|
| A01N 25/34 | (2006.01) | |
| A01N 25/10 | (2006.01) | |
| A01N 25/12 | (2006.01) | |
| A01N 33/12 | (2006.01) | |
| A01N 59/16 | (2006.01) | |
| A47L 13/17 | (2006.01) | |
| D04H 1/26 | (2012.01) | |
| D04H 1/28 | (2012.01) | |

(52) U.S. Cl.
CPC ............ *A01N 25/34* (2013.01); *A01N 25/10* (2013.01); *A01N 25/12* (2013.01); *A01N 33/12* (2013.01); *A01N 59/16* (2013.01); *A47L 13/17* (2013.01); *D04H 1/26* (2013.01); *D04H 1/28* (2013.01); *A01N 2300/00* (2013.01)

(58) Field of Classification Search
CPC ......... A61K 8/416; A01N 33/12; A01N 59/16
See application file for complete search history.

(56) References Cited

U.S. PATENT DOCUMENTS

| | | | |
|---|---|---|---|
| 6,559,116 B1 | 5/2003 | Godfroid et al. | |
| RE40,495 E | 9/2008 | Svendsen | |
| 8,486,427 B2 | 7/2013 | Colman et al. | |
| 2004/0031749 A1* | 2/2004 | Koslow | C02F 1/004 210/764 |
| 2010/0190004 A1* | 7/2010 | Gibbins | A61L 15/46 428/346 |
| 2011/0201534 A1* | 8/2011 | Ponder | C11D 1/62 510/516 |
| 2012/0135658 A1 | 5/2012 | Stone et al. | |
| 2016/0249606 A1 | 9/2016 | Hartgrove et al. | |
| 2017/0362551 A1* | 12/2017 | Merlet | C11D 3/3723 |
| 2018/0179470 A1* | 6/2018 | Saveyn | C11D 3/30 |

FOREIGN PATENT DOCUMENTS

| | | |
|---|---|---|
| EP | 2835419 A1 | 2/2015 |
| EP | 2835466 A1 | 2/2015 |
| KR | 101502404 B1 | 3/2015 |
| WO | WO 1998006260 A1 | 2/1998 |

* cited by examiner

*Primary Examiner* — Kyle A Purdy
(74) *Attorney, Agent, or Firm* — Laine IP Oy

(57) ABSTRACT

The current invention relates to modifying the surface of a cellulose-containing nonwoven substrate carrying a quaternary ammonium compound. A material for a nonwoven disinfecting wipe is provided which material includes a nonwoven substrate comprising cellulose and synthetic fibers and a combination of poly(vinylamine) and poly(amideamine-epichlorohydrin). Further, a method is provided for preparing a material for a nonwoven disinfecting wipe, the method comprising treating a nonwoven substrate comprising cellulose with poly(vinylamine) and poly(amideamine-epichlorohydrin).

18 Claims, 1 Drawing Sheet

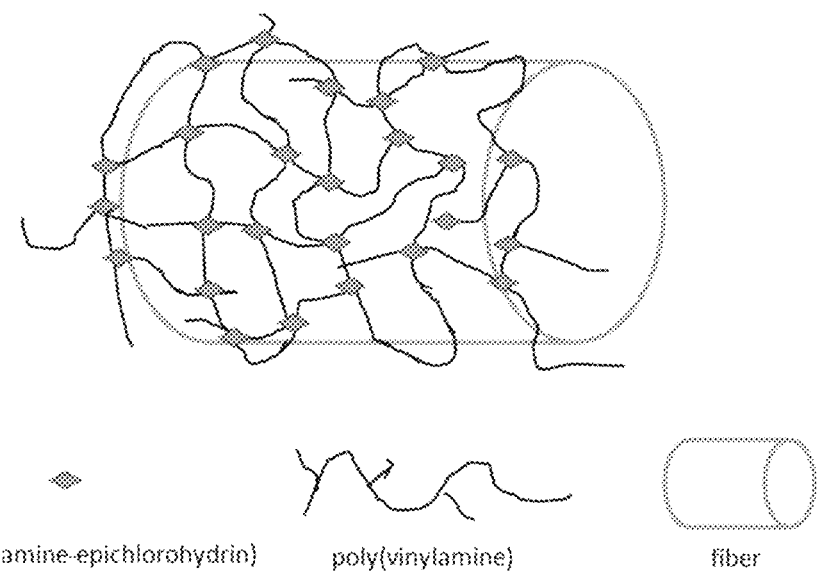

SUBSTRATE FOR EFFICIENT USE IN SANITIZING AND DISINFECTING

BACKGROUND OF THE INVENTION

An important area of application for nonwoven fabrics is in the field of wiping materials, also known as "wipes" or "wipers". Wipes are used for a large number of purposes in industrial, domestic, institutional and personal cleaning settings. Within these applications, a common requirement is that the wipe be absorbent towards water and aqueous solutions, or towards certain solvents in the case of industrial wipes. Wipes are often sold and packaged in a pre-moistened state as 'wet wipes'. Nonwoven disinfecting wipes are primarily composed of negatively charged cellulosic fibers such as wood pulp and viscose fibers, and comprise a liquid disinfectant. Such wipes are used for a wide variety of application, both for surface and skin disinfection. A problem with these products is often poor disinfectant delivery due to the fact that the cellulosic fibers bind and retain the active ingredient in the disinfectant solution. The disinfection solution with which the wipes are impregnated is often a positively charged disinfecting solution, typically comprised of quaternary ammonium compounds. During use, the wipe is compromised as the disinfecting solution is bound by the nonwoven fibers by electrostatic interactions. The disinfecting solution is not necessarily fully released to decontaminate the surfaces being cleaned. Up to 50% or more of the disinfecting solution can remain bound to the nonwoven substrate, which could be below the required quat level for disinfecting purposes.

Prior solutions developed to assist the release of quaternary ammonium compounds from the nonwoven wipe include the use of ionically charged binders in combination with or without surfactants. Recent solutions include the pretreatment of cellulose based nonwoven wipes with three-component formulations composed of a nonionic surfactant combined with small quaternary compounds such as tetramethylammonium chloride, and an electrolyte compound such as polyethylene oxide.

In U.S. Pat. No. 8,486,427 is disclosed an antimicrobial wipe formed from fibers having a negative surface charge (e.g. cellulose fibers), said wipe having an applied aqueous germicidal solution typically containing quaternary ammonium compounds. The wipe contains a polymer coating comprising high weight polyamideamine release agent. The release agent is able to adhere to the wipe, occupying binding sites and preventing the antimicrobial agent to adhere thereto.

In US patent application US 2016/0249606 is disclosed a wipe including at least one nonwoven layer, at least one pulp layer and a cationic additive. The layers may be hydroentangled, and the cationic additive may comprise a cationic polymer, e.g. a polyamine. The cationic additive prevents the quaternary ammonium compound from ionically attaching to the wipe.

In international patent application publication WO1998006260A1, silver based ions and particles are disclosed for use in antimicrobial compositions.

The prior art solutions have certain drawbacks. Solutions based on nonwovens containing ionically charged binders for repelling the quaternary ammonium disinfectants negatively impact the overall performance of the nonwoven wipe by decreasing its absorption capacity and adversely altering the mechanical properties that contribute to scrubbing and cleaning of hard surfaces. In particular, by increasing the stiffness of the nonwoven substrate and due to its film forming behavior, the binder-treated substrates tend to streak while in the process of cleaning hard surfaces and do not uniformly distribute the disinfecting solution.

Solutions based on the pre-treatment of the cellulosic disinfecting wipe with a nonionic surfactant in combination with an electrolyte and an additional quaternary compound tend to be expensive in material composition and do not easily lend themselves to industrial applications. Furthermore, nonionic surfactants can inhibit the overall disinfecting function of quaternary ammonium compounds by inducing micelle formation of the quaternary compound, and therefore not making it fully available for disinfection of the target surface.

It is the objective of the current invention to provide a solution that does not negatively impact the absorbency, cleaning, scrubbing and dirt pick-up properties of a disinfecting wipe, while providing a uniform and complete release of the disinfectant quaternary ammonium compound associated with the wipe. It was an additional objective of the invention to provide a solution that is not prone to disruption and/or loss of efficiency over time, especially as disinfecting wipes typically are stored wet with the disinfecting solution up to a year.

In addition, materials according to the invention were investigated for antimicrobial/disinfecting properties using silver nanoparticles.

It was an additional objective of the current invention to provide a cost effective solution in terms of raw materials and industrial application methods.

SUMMARY OF THE INVENTION

The current invention is based on modifying the surface of a cellulose-containing nonwoven substrate carrying a quaternary ammonium compound, to negate the electrostatic interactions between the positively charged (cationic) quaternary ammonium compound and the negatively (anionic) charged cellulose fibers. More specifically, a hydrogel composed of poly(vinylamine) (PVAm) a weakly cationic polymer bearing primary amine groups in the polymer backbone and poly(amideamine-epichlorohydrin) (PAE or PAAE), a water-soluble resin with reactive four-membered 3-hydroxyazetidium groups in a polyamideamine backbone, is applied to the cellulose-containing nonwoven. PAE is also considered a weak cationic.

According to a first aspect of the present invention, a material for a nonwoven disinfecting wipe is provided which material includes a nonwoven substrate comprising cellulose and synthetic fibers and a combination of poly(vinylamine) and poly(amideamine-epichlorohydrin).

Because of the reactivity of the PVAm primary amine groups, the blends of PVAm with PAE result in a covalent three dimensional network structured crosslinked hydrogel by means of a ring-opening coupling reaction at room temperature. By having PVAm in excess of PAE, the three dimensional network structured crosslinked hydrogel is additionally adsorbed onto the cellulose fibers as well as held firmly in place by the entanglement with the cellulose fibers with are highly hydroentangled with the base polypropylene spunbond. The absorption is induced by hydrogen bonding between the hydroxyl groups and the primary amine groups, resulting in a robust and permanent surface treatment. The robust surface treatment ensures the treatment is held together for a long period of time even if the material being used for multiple sanitization and disinfecting usage under high mechanical load such as scrubbing and cleaning or placed in quat solution for prolonged period of time.

According to a second aspect of the present invention, a method is provided for preparing a material for a nonwoven disinfecting wipe, the method comprising treating a nonwoven substrate comprising cellulose with poly(vinylamine) and poly(amideamine-epichlorohydrin).

The polymers may be applied by standard industrial means such as dip and squeeze, spray, foam coating or other standard coating processes.

Definitions

Nonwoven substrate: The nonwoven substrate referred to herein may be a composite made of cellulose fibers, like wood pulp, natural or man-made fibers, and continuous synthetic filaments that are entangled by different processes such as wetlaid, spunlace, needlepunch, knitting and various interlaid web processes. The continuous synthetic filaments are manufactured by processes such as spunbond, meltblown, or a combination of both (SMS).

Wood pulp: For the purposes of the current invention, the term wood pulp refers to natural cellulose fibers which are derived from wood.

Natural fibers: For the purposes of the current invention, natural fibers include but are not limited to cotton, hemp, flax, linen, bamboo, sisal, jute and kapok.

Man-made fiber: For the purposes of the current invention, the term man-made fibers refers to cellulose-based fibers which have undergone a dissolving and regeneration process. Examples are viscose and lyocell.

Synthetic filaments: The term "synthetic filaments" as used herein refers to products formed by polymerization of monomers. Examples include but not limited to be polypropylene, polyester, polyethylene, polylactic acid and/or co-polymers of these.

The hydroentanglement process referred to in the present description refers to interlaying, arranging, and mechanically bonding the fibers using high pressure jets of water.

The description of the essential features of the invention does not exclude the use of additional materials to enhance the performance of the invention. These materials could be catalysts, pigments, debonders, stabilizers, flow promoters etc.

BRIEF DESCRIPTION OF THE FIGURE

FIG. 1 is a schematic illustration of the three-dimensional network bonding between poly(vinylamine) and poly(amideamine-epichlorohydrin) around the cellulosic fiber.

DETAILED DESCRIPTION

A nonwoven web is pre-formed, preferably by a hydroentanglement process. According to the invention, the nonwoven web is provided with a cationic charged network formed by the two polymers poly(vinylamine) (PVAm)

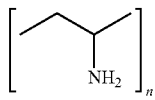

and poly(amideamine-epichlorohydrin) (PAE)

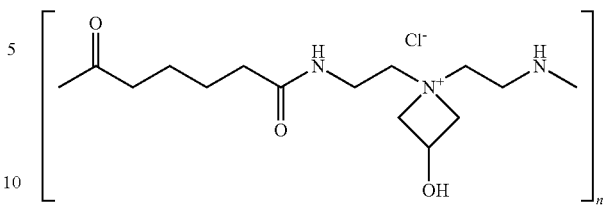

which are both cationic in charge and water soluble. PAE is formed by the reaction of a polyamideamine having secondary amine groups with epichlorohydrin. Part of the amine groups react with the epichlorohydrin giving rise to highly reactive aminochlorohydrin and azetidinium groups; part remains intact and renders the product cationic and soluble.

The reactive groups on PAE may react with the cellulose on the one hand, and with the amine groups of PVAm on the other hand. Thus, the two polymers crosslink to form a three-dimensional network with the cellulose fibers in the substrate. After forming the cationic three-dimensional network on its surface, the substrate can absorb and release positive charged quaternary ions efficiently. The substrate surface no longer neutralizes the charge on the quaternary compounds and helps in efficient release of quaternary compounds for sanitizing and disinfectant applications. The three-dimensional network will help by not neutralizing the positive quaternary ions and will also help in the repelling the cationic ions, resulting in better release of quaternaries for sanitizing and disinfectant applications. There is no significant change in the physical properties of the nonwoven web.

The nonwoven fabric forming the substrate can be a wetlaid or spunlace product.

Preferred quaternary ammonium compounds include but are not limited to alkyl didecyl dimethyl ammonium chloride, benzalkonium chloride, benzethonium chloride, benzyldimethylstearylammonium chloride, cetalkonium chloride, cetrimide, cetylpyridinium chloride, cetyltrimethylammonium bromide, dialkyl dimethyl ammonium chloride, dihydrotallow dimethyl ammonium chloride, ditallowdimethylammomium chloride, N-alkyl dimethyl ethylbenzyl ammonium chloride, and N-alkyl dimethylbenzyl ammonium chloride. Examples of other useful antimicrobial agents are alcohols, halogenated diphenyl ethers, phenolic compounds, phenoxy propanol, benzyl alcohol and chlorhexidine hydrochloride.

A preferred method of surface treatment is by blending the two components in an aqueous solution at room temperature and applying to the nonwoven substrate by a dip and squeeze coating technique such as a size-press to control the addition level, and subsequently drying the substrate to remove substantially all of the water. Preferable ratios of PVAm to PAE are 8:1, 4:1 and 3:1.

According to a further aspect of the invention, the PVAm/PAE hydrogel complex can be further functionalized with silver nanoparticles to render the substrate antimicrobial. Further functionalization can be also be achieved due to the reactive nature of the primary amine groups.

A recommended treatment level is in the range of 1 to 2% added weight on the final product to optimize performance in terms of quaternary compound release improvement, ease of coating application and minimizing raw material cost. The treated level could be from 1% to 100% of the weight of the final product depending on the substrate application.

FIG. 1 depicts the three dimensional network comprising the two polymers which are cross-linked together with a small section of fiber. When the nonwoven web is passed through the polymer solution of poly(vinylamine) and poly (amideamine-epichlorohydrin) which was already in the cross-linked state, the squeezing action of the size press enhances the impregnation of the polymer between the hydroentangled fibers. The polymer chains of the poly (vinylamine) and poly(amideamine-epichlorohydrin) encapsulate the fiber surface and are crosslinked three-dimensionally with each other due to the presence of amine groups. The FIGURE shows only a small portion of the web for clarity. However, the nonwoven web is completely covered with and intertwined with the poly(vinylamine) and poly (amideamine-epichlorohydrin) chains, which do not leach out even after storing the nonwoven web in quat solution for 8 hours.

EXAMPLES

The following non-limiting examples further illustrate the invention.

Example 1

An untreated 70 gsm nonwoven substrate was chosen which was made by hydro entangling 17 gsm polypropylene spunbond from Avgol and 53 gsm wood pulp—Grande Prairie (ECF—Elemental Chlorine Free) Northern Bleached Softwood pulp from Weyerhaeuser. The untreated substrate was treated with Kymene™ (Solenis) and Lupamin® 9095 (BASF) in a 1:4 ratio. Wipes prepared from the treated substrate were size pressed with a solution of Lupamin® (50 ml), Kymene™ (13 ml), water (1032 ml), and the pH of the solution was maintained at 10 by adding 25% NaOH (5 ml). The treated wipes were then dried using hot plate at 105° C. Both treated and untreated wipes were then tested to determine the quat release efficiency. A control quat solution of 800 ppm was made and added 4 times the weight of the dry untreated and treated wipes. The quat release efficiency was then titrated after 48 hours by squeezing 10 ml of quat solution from untreated and treated wipes. As shown in Table 1, the treated wipe showed 100% quat release efficiency after 48 hours as against untreated wipe which showed only 21% quat release efficiency. This result proves that this treatment can prevent the quat depletion over a period of time while maintaining a sufficient quat level for efficient disinfecting results.

TABLE 1

| Sample Name | Starting Quat ppm | Expressed after 48 hours | % Expressed |
| --- | --- | --- | --- |
| Untreated | 800 | 170 | 21 |
| Treated | 800 | 800 | 100 |

Example 2

In Example 2, 70 gsm wipes were prepared (Untreated) from substrate made by wet laid technology using 17 gsm polypropylene spunbond from Avgol and 53 gsm wood pulp—Grande Prairie (ECF—Elemental Chlorine Free) Northern Bleached Softwood pulp from Weyerhaeuser. The untreated wipe was treated with Kymene™ (from Solenis) and Lupamin® 9095 (from BASF) in 1:8 ratio. Wipes were size pressed with a solution of Lupamin® (100 ml), Kymene™ (13 ml), water (982 ml), with and without 5.5 ml of blue pigment (from Polysperse Corporation), and the pH of the solution was maintained at 10 by adding 25% NaOH (5 ml). The wipes were then dried using hot plate at 105° C. All treated, color treated and untreated wipes were then tested to determine the quat release efficiency. A control quat solution of 800 ppm was made and added 4 times the weight of the dry untreated, treated, and color treated wipes. The quat release efficiency was then titrated after 48 hours by squeezing 10 ml of quat solution from untreated, treated, and color treated wipes. As shown in Table 2, both the treated and color treated wipe showed 100% quat release efficiency after 48 hours as against untreated wipe which showed only 21% quat release efficiency. The result proves that this treatment can prevent the quat depletion over a period of time while maintaining a sufficient quat level for efficient disinfectant results.

TABLE 2

| Sample Name | Starting Quat ppm | Expressed after 48 hours | % Expressed |
| --- | --- | --- | --- |
| Untreated | 800 | 170 | 21 |
| Treated | 800 | 800 | 100 |
| Color Treated | 800 | 800 | 100 |

Example 3

In Example 3, 70 gsm wipes were prepared (Untreated) from substrate made by wet laid technology using 17 gsm polypropylene spunbond from Avgol and 53 gsm wood pulp—Grande Prairie (ECF—Elemental Chlorine Free) Northern Bleached Softwood pulp from Weyerhaeuser. The untreated wipes were sized pressed at different polymer concentrations using Kymene™ (from Solenis) and Lupamin® 9095 (from BASF) in 1:3 ratio. The pH of the treatment solution was maintained at pH 10 by adding 25% NaOH solution.

Treated A (10%)—The wipe was size pressed with a solution of Lupamin® (75 ml), Kymene™ (25 ml), water (900 ml), and the pH of the solution was maintained at 10 by adding 25% NaOH (5 ml).

Treated B (20%)—The wipe was size pressed with a solution of Lupamin® (150 ml), Kymene™ (50 ml), water (800 ml), and the pH of the solution was maintained at 10 by adding 25% NaOH (7 ml).

Treated C (30%)—The wipe was size pressed with a solution of Lupamin® (225 ml), Kymene™ (75 ml), water (700 ml), and the pH of the solution was maintained at 10 by adding 25% NaOH (12 ml).

The wipes were then dried using hot plate at 105° C. All treated and untreated wipes were tested to determine the quat release efficiency. A control quat solution of 550 ppm was made and tested with different treated and untreated wipes. 2 wipes approximately weighing 28 gm of each untreated and treated wipes were put in 2 liters of quat solution. After 15 min and 16 hrs, the wipes were taken out from the quat solution and excess solution was squeezed from the wipes. The wipes were then squeezed again for expressed solution (10 ml) in the titration container to determine the quat release efficiency. After 16 hrs, wipes were also tested to determine the quat depletion in the beaker due to the wipes. As shown in Table 3, the untreated wipe showed only 40% quat release efficiency as against treated wipes which were above 90% after 15 min. All the treated wipes showed 100% quat release efficiency after 16 hrs whereas untreated wipe showed only 45% quat release efficiency. The percent quat level in the beaker loaded with treated wipes after 16 hrs showed no decrease in the quat level against the untreated wipe.

TABLE 3

| Sample ID | Quat ppm | Expressed ppm from wipe after 15 min | % Expressed quat from wipe after 15 min | Expressed ppm from beaker after 16 hrs | % quat level in beaker after 16 hrs | Expressed ppm from wipe after 16 hrs | % Expressed quat from wipe after 16 hrs |
|---|---|---|---|---|---|---|---|
| Untreated | 550 | 220 | 40 | 270 | 49 | 250 | 45 |
| Treated-A | 550 | 520 | 95 | 550 | 100 | 550 | 100 |
| Treated-B | 550 | 530 | 96 | 550 | 100 | 550 | 100 |
| Treated-C | 550 | 550 | 100 | 550 | 100 | 550 | 100 |

Example 4

In Example 4, 70 gsm wipes were prepared (Untreated) from substrate made by wet laid technology using 17 gsm polypropylene spunbond from Avgol and 53 gsm wood pulp—Grande Prairie (ECF—Elemental Chlorine Free) Northern Bleached Softwood pulp from Weyerhaeuser. The untreated wipes were size pressed at different following polymers concentrations with the Kymene™ (from Solenis) and Lupamin® 9095 (from BASF) in 1:3 ratio. The pH of the treatment solution was maintained at pH 10 by adding 25% NaOH solution.

Treated A (10%)—The wipe was size pressed with a solution of Lupamin® (75 ml), Kymene™ (25 ml), water (900 ml), and the pH of the solution was maintained at 10 by adding 25% NaOH (5 ml).

Treated B (20%)—The wipe was size pressed with a solution of Lupamin® (150 ml), Kymene™ (50 ml), water (800 ml), and the pH of the solution was maintained at 10 by adding 25% NaOH (7 ml).

Treated C (30%)—The wipe was size pressed with a solution of Lupamin® (225 ml), Kymene™ (75 ml), water (700 ml), and the pH of the solution was maintained at 10 by adding 25% NaOH (12 ml).

The wipes were then dried using hot plate at 105° C. All treated and untreated wipes were tested to determine the quat release efficiency. Quat solutions of 3320 ppm to 3440 ppm were made and tested with different treated and untreated wipes. These quat solutions were used to lotionize the wipes and were added at 4 times the weight of the dry treated and untreated wipes. The quat release efficiency was then titrated after 72 hours by squeezing 10 ml of quat solution from untreated and treated wipes. As shown in Table 4, the treated wipes (B and C) showed 100% quat release efficiency after 72 hours against untreated wipe which showed only 32-34% % quat release efficiency. This result proves that this treatment can prevent the quat depletion after 72 hours while maintaining sufficient quat levels for efficient disinfecting results.

TABLE 4

| Sample ID | Starting Quat Conc (ppm) | Expressed ppm from wipe after 72 hours | % Expressed quat from wipe after 72 hrs |
|---|---|---|---|
| Untreated | 3440 | 1090 | 32 |
| Treated-A | 3440 | 3000 | 87 |
| Untreated | 3250 | 1090 | 34 |
| Treated-B | 3250 | 3320 | 102 |
| Untreated | 3220 | 1045 | 32 |
| Treated-C | 3220 | 3350 | 104 |

Example 5

In Example 5, 70 gsm wipes were prepared (Untreated) from substrate made by wet laid technology using 17 gsm polypropylene spunbond from Avgol and 53 gsm wood pulp—Grande Prairie (ECF—Elemental Chlorine Free) Northern Bleached Softwood pulp from Weyerhaeuser. The untreated wipes were sized pressed at varying polymers concentrations with Kymene™ (from Solenis) and Lupamin® 9095 (from BASF) in 1:3 ratio. The pH of the treatment solution was maintained at pH 10 by adding 25% NaOH solution. Treated (20%)—wipe was size pressed with a solution of Lupamin® (150 ml), Kymene™ (50 ml), water (800 ml), and the pH of the solution was maintained at 10 by adding 25% NaOH (7 ml). The treated wipe was then dried using hot plate at 105 degree C. All treated and untreated wipes were then tested to determine the quat release efficiency. A control quat solution of 400 ppm was made and tested with different treated and untreated wipes. 10 wipes each, approximately weighing 14 gm, of untreated and treated wipes were put in 10 liters of quat solution. After every hour over a period of total 5 hours, 2 wipes were taken out from the quat solution and excess solution was squeezed from the wipes. The wipes were then squeezed again for expressed solution (10 ml) in the titration container to determine the quat release efficiency. Those wipes were kept aside and not put again in the quat solution. At the same time, after every hour, wipes were also tested to determine the quat depletion in the beaker due to the wipes. As shown in Table 5, after 5 hours, the expressed quat of treated wipe was significantly higher than untreated wipes, maintaining a sufficient level of quat for disinfecting purposes.

TABLE 5

| Sample Name | Hours | Starting Quat ppm | Expressed ppm from wipe | Expressed ppm from beaker |
|---|---|---|---|---|
| Untreated | 1 | 400 | 210 | 250 |
|  | 2 | 400 | 230 | 250 |
|  | 3 | 400 | 230 | 250 |
|  | 4 | 400 | 210 | 330 |
|  | 5 | 400 | 190 | 300 |
| Treated | 1 | 400 | 390 | 330 |
|  | 2 | 400 | 450 | 380 |
|  | 3 | 400 | 420 | 360 |
|  | 4 | 400 | 320 | 400 |
|  | 5 | 400 | 300 | 310 |

The invention claimed is:
1. A nonwoven material comprising:
   a nonwoven fibrous substrate comprising cellulosic fibers and synthetic fibers;
   a cross-linked polymeric network comprising a polyvinylamine polymer and a poly(amideamine-epichlorohydrin) polymer that encapsulates the cellulosic fibers of the nonwoven fibrous substrate; and
   a solution of a cationic antimicrobial compound comprising quaternary ions in direct contact with an entirety of the cross-linked polymeric network, wherein the cross-linked polymeric network is functionalized with silver nanoparticles.

2. The nonwoven material of claim 1, wherein the cross-linked polymeric network consists of the polyvinylamine polymer and the poly(amideamine-epichlorohydrin) polymer.

3. A process for preparing a nonwoven material comprising:
   treating a nonwoven fibrous substrate comprising cellulosic fibers and synthetic fibers with a mixture of a polyvinylamine polymer and a poly(amideamine-epichlorohydrin) polymer, to form a cross-linked polymeric network consisting of the polyvinylamine polymer and the poly(amideamine-epichlorohydrin) polymer that encapsulates the cellulosic fibers of the nonwoven fibrous substrate;
   after the treating, drying the nonwoven fibrous substrate, and
   after the drying, contacting an entirety of the cross-linked polymeric network with a solution of a cationic antimicrobial compound to maintain the cationic antimicrobial compound within the nonwoven fibrous substrate and the cross-linked polymeric network.

4. The process of claim 3, wherein the cross-linked polymeric network improves release of the solution of the cationic antimicrobial compound from the nonwoven fibrous substrate relative to a nonwoven fibrous substrate without the cross-linked polymeric network.

5. The process of claim 3, wherein the solution of the cationic antimicrobial compound comprises a quaternary ammonium compound.

6. The process of claim 3, wherein the cellulosic fibers and the synthetic fibers are hydroentangled.

7. The process of claim 3, wherein, during the treating, the polyvinylamine polymer is present in an amount greater than an amount of the poly(amideamine-epichlorohydrin) polymer.

8. A nonwoven material comprising:
   a nonwoven fibrous substrate comprising cellulosic fibers and synthetic fibers;
   a cross-linked polymeric network consisting of a polyvinylamine polymer and a poly(amideamine-epichlorohydrin) polymer incorporated into the nonwoven fibrous substrate; and
   a solution of cationic antimicrobial compound comprising quaternary ions in direct contact with an entirety of the cross-linked polymeric network.

9. The nonwoven material of claim 8, wherein the cross-linked polymeric network improves release of the solution of the cationic antimicrobial compound from the nonwoven fibrous substrate during use relative to a nonwoven fibrous substrate without the cross-linked polymeric network.

10. The nonwoven material of claim 8, wherein the solution of the cationic antimicrobial compound comprises a quaternary ammonium compound.

11. The nonwoven material of claim 8, wherein the synthetic fibers are selected from the group consisting of polypropylene, polyester, polylactic acid, polyethylene terephthalate, and glass.

12. The nonwoven material of claim 8, wherein the cellulosic fibers are selected from the group consisting of wood pulp, viscose, rayon, cotton, hemp, jute, and flax.

13. The nonwoven material of claim 8, wherein the cellulosic fibers and the synthetic fibers are hydroentangled.

14. The nonwoven material of the claim 8, where the nonwoven material has a basis weight of 25-120 gsm.

15. The nonwoven material of claim 8, wherein the cross-linked polymeric network is functionalized with silver nanoparticles.

16. The nonwoven material of claim 8, wherein the polyvinylamine polymer is present in an amount greater than an amount of the poly(amideamine-epichlorohydrin) polymer.

17. The nonwoven material of claim 8, wherein a ratio of the polyvinylamine polymer to the poly(amideamine-epichlorohydrin) polymer is from 3:1 to 8:1.

18. The nonwoven material of claim 8, wherein at least 94% of the solution of the cationic antimicrobial compound is capable of being released from the nonwoven fibrous substrate after 15 minutes.

* * * * *